(12) United States Patent
Reed

(10) Patent No.: US 6,469,308 B1
(45) Date of Patent: Oct. 22, 2002

(54) ULTRAVIOLET RADIATED WATER TREATMENT TANK

(76) Inventor: Ryan M. Reed, P.O. Box 652, Chatsworth, GA (US) 30705

(*) Notice: Subject to any disclaimer, the term of this patent is extended or adjusted under 35 U.S.C. 154(b) by 1 day.

(21) Appl. No.: 09/845,493

(22) Filed: May 1, 2001

(51) Int. Cl.⁷ .............................. C02F 1/32; A61L 2/10
(52) U.S. Cl. ................ 250/436; 250/437; 250/438; 250/372; 250/373; 250/365; 250/504 R; 422/186.3; 422/24
(58) Field of Search ................ 250/436, 437, 250/373, 438, 365, 372, 504 R; 422/186.3, 24

(56) References Cited

U.S. PATENT DOCUMENTS

| | | | |
|---|---|---|---|
| 2,738,427 A | 3/1956 | Wagnon | 250/48 |
| 3,767,918 A | * 10/1973 | Graybeal | 250/433 |
| 4,322,291 A | 3/1982 | Ho | 210/181 |
| 4,969,991 A | 11/1990 | Valadez | 210/96.2 |
| 5,302,356 A | 4/1994 | Shadman | 422/186.3 |
| 5,441,179 A | 8/1995 | Marsh | 222/180 |
| 5,744,028 A | 4/1998 | Goto | 210/181 |
| 6,077,427 A | 6/2000 | Burrows | 210/198.1 |
| 6,099,799 A | 8/2000 | Anderson | 422/24 |
| 6,139,726 A | * 10/2000 | Greene | 210/94 |

FOREIGN PATENT DOCUMENTS

| | | | |
|---|---|---|---|
| GB | 1 459 395 | 12/1976 | |
| GB | 2 022 979 A | 12/1979 | C02B/3/02 |
| JP | 9-128641 | 5/1997 | G07F/13/00 |
| JP | 10-337567 | 12/1998 | C02F/1/32 |

* cited by examiner

Primary Examiner—John R. Lee
Assistant Examiner—Nikita Wells
(74) Attorney, Agent, or Firm—Richard C. Litman

(57) ABSTRACT

An ultraviolet radiation water treatment device for a water cooler machine having an ultraviolet lamp housed inside a transparent inner sleeve which is itself disposed inside an outer transparent sleeve. The upper ends of the two sleeves are housed in a short pipe having a peripheral flange which abuts the sides of the cooler's water tank. A water inlet tube enters the top of the tank and passes between the two sleeves to feed water proximate the tank bottom to circulate the influent water up between the two sleeves and down outside the outer sleeve into the reservoir water to accomplish three exposure passes to the bactericidal ultraviolet radiation.

17 Claims, 1 Drawing Sheet

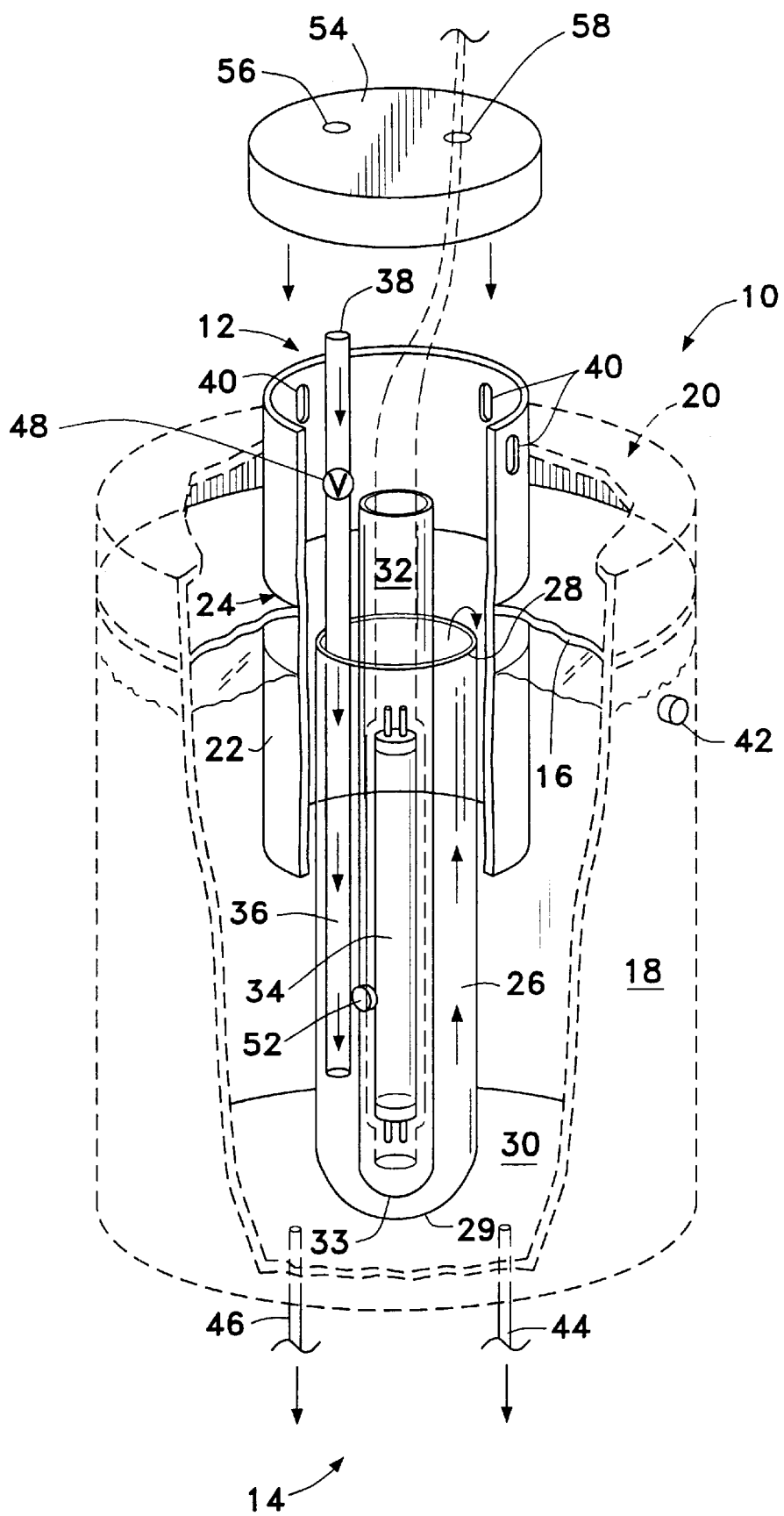

ULTRAVIOLET RADIATED WATER TREATMENT TANK

BACKGROUND OF THE INVENTION

1. Field of the Invention

The present invention relates generally to water purifying devices. More specifically, the invention is an ultraviolet radiated water purifier device for a water cooler reservoir.

2. Description of the Related Art

The related art of interest describes various water purifying devices, but none describes the present invention. There is a need for a water purifying device installable in a water cooler tank which will be fully effective without producing a burnt water taste. The related art will be discussed in the order of perceived relevance to the present invention.

U.S. Pat. No. 6,099,799 issued on Aug. 8, 2000 for Ellis D. Anderson, describes an apparatus for ultraviolet disinfection of water comprising the treatment of untreated and treated water in separate streams in the apparatus, in which the streams separately enter and exit the apparatus. An ultraviolet lamp inside a first sleeve emits rays through first and second ultraviolet transparent sleeves having an annular space therebetween to form an inner flow channel and an annular space between the second sleeve and an ultraviolet resistant pressure vessel. The apparatus is distinguishable for structure required for treating both treated and untreated water in separate streams.

U.S. Pat. No. 4,322,291, issued on Mar. 30, 1982 for Kuo-Sheng Ho, describes a hot water dispenser with a water purifier and an ultraviolet tank controlled by a synchronous valve system. The ultraviolet tank receives filtered water from the purifier tank, which filtered water passes through four vertical concentric transparent plates irradiated by the ultraviolet lamp in a protecting tube emitting light at a wavelength of 2537 Angstroms and positioned horizontally to traverse the tank. The ultraviolet tank system is distinguishable for its structural arrangement of the lamp and the transparent plates.

U.S. Pat. No. 2,738,427, issued on Mar. 13, 1956 for William N. Wagnon, describes a water purifier apparatus comprising a cylindrical casing having a highly reflective inner surface, an ultraviolet ray tube along the axis of the casing, and a water conduit having a plurality of transparent quartz portions parallel to the tube. The apparatus is distinguishable for its serpentine pipe system within the casing.

U.S. Pat. No. 5,302,356, issued on Apr. 12, 1994 for Farhang F. Shadman et al., describes an ultrapure water treatment system for producing water for cleaning integrated circuit chips comprising a vertical tank containing a vertically oriented ultraviolet lamp emitting a wavelength of 180–190 nanometers. Water enters and exits through catalytic filters containing photoactive catalysts such as the oxides of titanium, zinc, tungsten, tin, copper and cadmium sulfide or selenide on porous substrates such as stainless steel, glass, and the like. The system is distinguishable for requiring catalysts.

U.S. Pat. No. 5,441,179, issued on Aug. 15, 1995 for Stephen A. Marsh, describes an ultraviolet disinfecting device installed in a water cooler holding tank. A bottle positioning collar having a transparent window incorporates an ultraviolet lamp which periodically exposes the water in the holding tank. The device is distinguishable for its collar structure.

U.K. Patent Application No. 2 022 979 A, published on Dec. 19, 1979, describes the purification of water from a water cooler container by adding an annular ultraviolet lamp around or below the neck of the inverted water bottle. The apparatus is distinguishable for being limited to one location where water flows from the reservoir.

U.S. Pat. No. 5,744,028, issued on Apr. 28, 1998 for Nobutaka Goto et al., describes a water treating apparatus comprising an electrolytic cell including an anode, a cathode and a three-dimensional carbon electrode in between. The electrolytic cell is provided downstream of a water tank. The apparatus is distinguishable for requiring electrolytic treatment.

U.S. Pat. No. 6,077,427, issued on Jun. 20, 2000 for Bruce D. Burrows, describes a water vending machine provided with a water purification system including a purification unit containing an ultraviolet lamp generating ozone gas which is directed on an intermittent or continuous basis against a dispenser nozzle. The water purification system is distinguishable for its limitation to an ultraviolet lamp in a tank.

U.S. Pat. No. 4,969,991, issued on Nov. 13, 1990 for Gerardo M. Valadez, describes a vending system for providing purified water comprising a microbial sterilizer utilizing ultraviolet radiation and other purification systems such as an activated carbon filter, an ion exchange resin bed, and a reverse osmosis filter. The vending system is distinguishable for its recirculating system involving sundry purification techniques.

Gt. Britain Patent Application No. 1 459 395, published on Dec. 22, 1976 for John E. Hunt et al., describes an ultraviolet sterilizer device comprising a mercury vapor discharge lamp for forming ultraviolet radiation and employing a solenoid valve for water flow control in the system. The sterilizing process involves the emission of ultraviolet light through a quartz safety jacket to radiate the flowing turbulent water in the metal jacket. The radiation impinges also on a layer of magnesium fluoro germinate to convert the emitted wavelength of light to red light. A silicon photo sensor cell converts the red light into a D.C. voltage to provide current for other electronic devices. The sterilizer device is distinguishable for its required manifold electronic devices.

Japan Patent Application No. 9-128641, published on May 16, 1997, describes an automatic sterilizing apparatus comprising a water tank containing a vertical ultraviolet lamp projecting downward from the lid, a push plate on the lid connected to a float, a protect switch on the lid, a high water level switch, a low water level switch, an internal overflow conduit, a water intake on the lid, and a water outlet on the bottom of the tank. A radiation level of 200 to 300 nanometers wavelength is used. The apparatus is distinguishable for its unprotected ultraviolet lamp.

Japan Patent Application No. 10-337567, published on Dec. 12, 1998, describes an ultraviolet lamp in a water cooler outside the water dispenser body for purifying water flowing in a U-shaped pipeline. The lamp is vertically located between a U-shaped transparent resin pipeline. The device is distinguishable for its simplified structure.

None of the above inventions and patents, taken either singularly or in combination, is seen to describe the instant invention as claimed. Thus, a ultraviolet water treatment solving the aforementioned problem of eliminating a burnt taste is desired.

SUMMARY OF THE INVENTION

The present invention is directed to an ultraviolet (UV) radiated water purifier device for a water cooler reservoir and the like. The purifier device operates inside a conventional cooler reservoir tank. A vertical pipe is centered in a horizontal flange or shield and contains air passage vents proximate its upper end to radiate any generated heat by the use of the UV lamp. The pipe and shield are made of an UV resistant material such as stainless steel to protect any non-ultraviolet resistant components that may degrade under exposure to UV light. The edge of the circular horizontal shield abuts the wall of the water reservoir or tank. A transparent outer tubular sleeve made of quartz in the shape of a test tube is contained within the pipe section of the shield and extends down into the cooler reservoir.

Contained within the outer transparent sleeve is a transparent inner tubular test tube shaped sleeve which extends beyond the mouth of the outer sleeve and contains the purifying UV lamp. The shield is above the normal water level to prevent stagnant air from contacting the water and the UV lamp, and prevents the air from transferring a burnt taste to the water.

A thin translucent water inlet tube made of a material such as polytetrafluoroethylene feeds water into the purifier and extends downward between the outer and inner sleeves. The water flows downward in the water inlet tube past the ultraviolet lamp for a first exposure pass and up between the two sleeves for a second exposure pass. The water overflows the outer sleeve and flows downward for a third exposure pass. Water inside the reservoir outside the sleeves is constantly exposed to an ultraviolet radiation passing through the translucent inlet tube and the two transparent sleeves.

The outer translucent sleeve retains much of the heat generated by the emitted ultraviolet light as an advantage to shorten the time period before the UV lamp becomes effective for killing any bacteria present such as heterotrophic bacteria, because the UV lamp must reach a specific temperature before it can effectively inactivate any bacteria present. A benefit in dissipating residual generated heat is a result of having the air vents in the pipe to conduct away the heat. The outer translucent sleeve helps to insulate the water in the cooler reservoir from the heat generated by the ultraviolet lamp, and thus aiding to protect the cooling mechanism. This heat mitigating effect results in an advantage in increasing the life of the conventional refrigeration components of a cooler apparatus.

Float switches or liquid level control probes are means included in the apparatus to control the water level within the cooler tank by a solenoid in the water inlet line. When the water level in the tank drops due to cooler water use, the normally closed solenoid is energized by the float switch or liquid level control probes to open and allow water to enter the treatment tank.

The water level monitoring devices also activate a timer which controls the ultraviolet lamp. Once activated the timer will illuminate the ultraviolet lamp for a preset period of time. The status of the ultraviolet lamp is monitored by an optical sensor in that in the event of a failure an audible alarm will sound or a light alarm will signal. The cooler reservoir container can also be coated with a material to inhibit the deleterious effects of ultraviolet radiation.

Accordingly, it is a principal object of the invention to provide a water purification system for a conventional water cooler machine having a water reservoir and a refrigeration system.

It is another object of the invention to provide a water purification system within a water cooler reservoir.

It is a further object of the invention to provide a water purification system utilizing an ultraviolet lamp within two transparent test tube sleeves inside the water cooler reservoir.

Still another object of the invention is to provide a water purification system having a shield structure for dissipating heat generated by the irradiation system.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWING

The sole FIGURE is a partially broken away, perspective view of an ultraviolet radiation water treatment tank according to the present invention.

DETAILED DESCRIPTION OF THE PREFERRED EMBODIMENTS

The present invention, as shown in the sole FIGURE, is directed to an ultraviolet radiation water treatment apparatus 10. The apparatus 10 works inside a conventional water cooler reservoir 18 with a pipe connection 12 for influent water and a pipe connection 14 for effluent water. An apertured circular ultraviolet radiation resistant shield 16 made of a material opaque to UV radiation such as stainless steel plate is disposed horizontally in the tank or reservoir 18 (shown in shadow as being not part of the invention) with its periphery abutting an inside surface of the sidewall and proximate an upper wall 20 of tank 18.

A short vertical pipe 22, also made of UV opaque material such as stainless steel plate, extends through a centered aperture 24 of the shield 16 and the upper wall 20 of the tank 18 with a cap 54 sealing the top end of the pipe 22. The bottom half of the pipe 22 is submerged in water in order to prevent stagnant air from being exposed to both water and the ultraviolet lamp. This is a critical point in the present invention, since this prevents the air above the water level in the reservoir 18 from being burnt by the UV radiation imparting a burnt taste to the circulating treated water in the reservoir 18.

A vertical transparent cylindrical outer sleeve 26 in the shape of a test tube and made of quartz has a top edge 28 proximate the level of the shield 16, and the domed bottom end 29 abuts a bottom surface or wall 30 of the tank 18, and is centered within the shield pipe 22. A vertical transparent cylindrical inner sleeve 32 having a similar domed end 33, which may also be made of quartz, is centered within the outer sleeve 26 and defines an annular flow channel. The inner sleeve 32 has a top edge extending above the shield 16 and the domed bottom end 33 is proximate the domed bottom end 29 of outer sleeve 26 allowing for flow between the two bottom ends 29 and 33.

A cylindrical ultraviolet lamp 34 is energized to radiate germicidal rays and is housed within the inner sleeve 32. The wiring (shown in dashed lines) for the UV lamp 34 passes upward inside the sleeve 32 and out the aperture 58 in the cap 54. A narrow cylindrical translucent water inlet tube 36 made of Teflon® (polytetrafluoroethylene) enters the cap 54 of the tank 10 through aperture 56 feeding influent water 38 into the reservoir and extends downward in the annular space between the outer sleeve 26 and the inner sleeve 32 to discharge influent water 38 proximate the bottom domed end 29 of the outer sleeve 26.

A water effluent pipe 44 feeding a hot water tank conventionally provided and another effluent pipe 46 feeding a cold water tank conventionally provided in the cooler apparatus pass through the bottom wall 30 of the tank 18. The influent water 38 enters the tank 18 via the water inlet tube 36 and circulates upward in the annular flow channel between the transparent outer sleeve 26 and inner sleeve 32 and downward between the outer sleeve 26 and the shield pipe 22 into the reservoir 18 to effect at least three passes proximate the ultraviolet lamp 34 in order to expose any harmful microorganisms in the water to the germicidal effects of UV radiation.

The shield pipe 22 has a plurality of equally spaced vents 40 above the shield 16 for exhausting heat from the purifier apparatus 10. A liquid level sensor device 42 is located on an outside surface of the tank 18 to regulate the quantity of water in order to keep the water level above the bottom end of the shield pipe 22 and to cut off the flow of influent water 38 when the water level exceeds a predetermined level. The liquid level sensor device 42 can be a conventional float switch or a liquid level control probe. A normally closed solenoid valve 48 is inserted in the influent pipe 12 to open to replace water being depleted as indicated by the liquid level sensor device 42. When the water level rises to the predetermined level, the level control sensor device 42 de-energizes the solenoid valve 48 to the normally closed state to cut off the inflow of water.

The sensor device 42 also activates a timer 50 to illuminate the lamp 34 for a preset time period. The lamp's operating time is an independent function activated by the sensor device 42. Once the timing cycle of the lamp 34 is activated, the lamp will light for the preset time period. Reactivation of the sensor device 42 due to water being dispensed from the cooler reservoir within the preset period of lamp operation will only result in activation of the solenoid 48, and not affect the lamp 34.

The status of the ultraviolet lamp 34 inside the tank 18 is monitored by an optical sensor 52 mounted on the inner sleeve 32, which sensor will either sound an alarm or illuminate a warning lamp to indicate when the lamp 34 fails to illuminate when required to by the liquid level sensor device 42.

An effluent pipe 44 is located below the reservoir outside the radius of outer sleeve 26. It is also contemplated that the inner surface of tank 18 can be coated with any material which would inhibit the effects of the ultraviolet lamp 34 such as a ceramic, or alternatively, the tank 18 can be made of stainless steel.

Thus, an effective water treatment tank can be incorporated in a water cooler apparatus to ensure the purification of drinking water without the burnt taste of the prior art devices by circulating the influent water to repeated exposure to the bacteria killing rays of a ultraviolet ray lamp. Control devices inside or attached to the treatment tank regulate safe operation of the water treatment tank.

It is to be understood that the present invention is not limited to the embodiments described above, but encompasses any and all embodiments within the scope of the following claims.

I claim:

1. An ultraviolet radiation water treatment device for a water cooler tank comprising:

a shield plate having a disk shape adapted for attachment to a side wall of a water cooler tank;

a shield pipe extending through the center of said shield plate, the pipe having an upper end, the pipe being adapted for extending through a top wall of a water cooler tank, said shield pipe being made from a material opaque to UV radiation;

a circular cap attached to the upper end of said shield pipe, the cap having an aperture defined therein;

an outer, cylindrical, transparent sleeve having a closed, dome-shaped lower end and an open upper end disposed in said shield pipe, said outer sleeve and said shield pipe defining an outer annular flow channel;

a cylindrical, transparent inner sleeve disposed within said outer sleeve and having a closed, dome-shaped lower end and an upper end extending above said outer sleeve, said inner sleeve and said outer sleeve defining an inner annular flow channel;

an ultraviolet lamp emitting ultraviolet light at a frequency having germicidal effect disposed within said inner sleeve; and a translucent water inlet tube extending through the aperture defined in said cap, the water inlet tube extending between said outer sleeve and said inner sleeve, the water inlet tube having a discharge opening proximate the lower end of said outer sleeve;

wherein influent water enters the water treatment device through said water inlet tube, is discharged proximate the lower end of said outer sleeve, flows upward through said inner annular flow channel, then downward through said outer annular flow channel into a water cooler tank in order to effect at least three passes proximate the ultraviolet ray lamp, whereby influent water is exposed to germicidal ultraviolet radiation for an extended time.

2. The ultraviolet radiation water treatment device according to claim 1, wherein said shield pipe has a plurality of vents defined therein above said shield plate for exhausting heat.

3. The ultraviolet radiation water treatment device according to claim 1, further comprising a liquid level sensor device disposable on the cylindrical upper wall of the tank to regulate a quantity of water above the lower end of said shield pipe.

4. The ultraviolet radiation water treatment device according to claim 3, wherein the liquid level sensor device is a float switch.

5. The ultraviolet radiation water treatment device according to claim 3, wherein the liquid level sensor device is a liquid level control probe.

6. The ultraviolet radiation water treatment device according to claim 1, further comprising at least one effluent pipe adapted for attachment to the bottom wall of the tank outside the radius of said outer sleeve.

7. The ultraviolet radiation water treatment device according to claim 1, wherein said water inlet tube is made of polytetrafluoroethylene.

8. The ultraviolet radiation water treatment device according to claim 1, wherein said inner and outer sleeves are made from quartz.

9. The ultraviolet water radiation treatment device according to claim 1, wherein the ultraviolet ray resistant shield and shield pipe are made of stainless steel.

10. The ultraviolet radiation water treatment device according to claim 1, further comprising a normally closed solenoid valve inserted in said water inlet tube.

11. The ultraviolet radiation water treatment device according to claim 1, further comprising a timer device connected to said ultraviolet lamp for controlling the illumination period of said ultraviolet ray lamp.

12. The ultraviolet radiation water treatment device according to claim 1, further comprising an optical sensor device attached to said inner sleeve, the optical sensor being disposed to sense ultraviolet light emitted by said ultraviolet lamp and for sensing when said ultraviolet ray lamp has malfunctioned.

13. The ultraviolet radiation water treatment device according to claim 1, further comprising a water cooler tank having a top wall, the water treatment device being disposed within the water cooler tank with said shield pipe extending through the top wall, the upper end of the shield pipe being disposed above the top wall.

14. The ultraviolet radiation water treatment device according to claim 13, wherein said water cooler tank has an inner surface coated with a ceramic composition.

15. The ultraviolet radiation water treatment device according to claim 13, wherein said water cooler tank is made of stainless steel.

16. The ultraviolet radiation water treatment device according to claim 13, wherein said water cooler tank is made of an ultraviolet radiation resistant material.

17. The ultraviolet radiation water treatment device according to claim 1, wherein said water inlet tube and said inner and outer sleeves are made from a material having a high transmittance to UV radiation.

\* \* \* \* \*